US010574934B2

(12) United States Patent
Sato

(10) Patent No.: US 10,574,934 B2
(45) Date of Patent: Feb. 25, 2020

(54) ULTRASOUND OBSERVATION DEVICE, OPERATION METHOD OF IMAGE SIGNAL PROCESSING APPARATUS, IMAGE SIGNAL PROCESSING METHOD, AND COMPUTER-READABLE RECORDING MEDIUM

(71) Applicant: OLYMPUS CORPORATION, Tokyo (JP)

(72) Inventor: Tomoya Sato, Tokorozawa (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/167,684

(22) Filed: Oct. 23, 2018

(65) Prior Publication Data

US 2019/0058844 A1 Feb. 21, 2019

Related U.S. Application Data

(63) Continuation of application No. PCT/JP2017/014867, filed on Apr. 11, 2017.

(30) Foreign Application Priority Data

May 24, 2016 (JP) .................. 2016-103532

(51) Int. Cl.
  *H04N 5/58* (2006.01)
  *A61B 1/045* (2006.01)
  (Continued)

(52) U.S. Cl.
  CPC .......... *H04N 5/58* (2013.01); *A61B 1/00009* (2013.01); *A61B 1/045* (2013.01); *G02B 23/24* (2013.01);
  (Continued)

(58) Field of Classification Search
  CPC combination set(s) only.
  See application file for complete search history.

(56) References Cited

U.S. PATENT DOCUMENTS 6,343,158 B1  1/2002 Shiohara
2009/0066787 A1  3/2009 Yamazaki
(Continued)

FOREIGN PATENT DOCUMENTS

JP  H10-232927 A  9/1998
JP  2007-180718 A  7/2007
(Continued)

OTHER PUBLICATIONS

International Search Report dated Jul. 4, 2017 issued in International Application No. PCT/JP2017/014867.
(Continued)

*Primary Examiner* — Janese Duley
(74) *Attorney, Agent, or Firm* — Scully, Scott, Murphy & Presser, P.C.

(57) ABSTRACT

An image signal processing apparatus includes: circuitry including: a mode setting circuitry configured to change a mode to one of a first mode and a second mode; a dividing circuitry configured to divide an input image signal into a base component signal and a detail component signal when the mode setting circuitry sets the first mode; a first tone compressing circuitry configured to perform a tone compression process on the base component signal to generate a compressed base component signal; a synthesizing circuitry configured to generate a synthetic image signal based on the detail component signal and the compressed base component signal; and a second tone compressing circuitry configured to perform a tone compression process such that tone of the input image signal becomes approximately equal to
(Continued)

tone of the compressed base component signal when the mode setting circuitry sets a second mode.

7 Claims, 7 Drawing Sheets

(51) Int. Cl.

| | | |
|---|---|---|
| *G02B 23/24* | (2006.01) | |
| *H04N 5/225* | (2006.01) | |
| *H04N 5/232* | (2006.01) | |
| *H04N 5/235* | (2006.01) | |
| *H04N 19/186* | (2014.01) | |
| *A61B 1/00* | (2006.01) | |
| *A61B 1/05* | (2006.01) | |
| *A61B 1/06* | (2006.01) | |

(52) U.S. Cl.
CPC ......... *H04N 5/2256* (2013.01); *H04N 5/2351* (2013.01); *H04N 5/2354* (2013.01); *H04N 5/23245* (2013.01); *H04N 19/186* (2014.11); *A61B 1/05* (2013.01); *A61B 1/06* (2013.01); *H04N 2005/2255* (2013.01)

(56) References Cited

U.S. PATENT DOCUMENTS

| | | | |
|---|---|---|---|
| 2012/0106867 A1 | 5/2012 | Yamada et al. | |
| 2014/0184916 A1* | 7/2014 | Steiner | G06T 5/007 |
| | | | 348/607 |
| 2015/0221087 A1 | 8/2015 | Houjou et al. | |
| 2015/0374210 A1* | 12/2015 | Durr | A61B 1/041 |
| | | | 600/111 |
| 2017/0148165 A1 | 5/2017 | Houjou et al. | |

FOREIGN PATENT DOCUMENTS

| | | |
|---|---|---|
| JP | 2009-100936 A | 5/2009 |
| JP | 2012-108898 A | 6/2012 |
| JP | 5159904 B2 | 3/2013 |
| JP | 2015-164512 A | 9/2015 |
| WO | 2007/129570 A1 | 11/2007 |

OTHER PUBLICATIONS

Japanese Office Action dated Jun. 7, 2018 in Japanese Patent Application No. 2017-561436.

Sato, K., "Contrast Improvement for a Linear/Log CMOS Image sensor", Konica Minolta Technology Report, 2007, pp. 82-87 (cited in ISR).

Land, E.H. et al., "Lightness and Retinex Theory", Journal of the Optical Society of America, Jan. 1971, vol. 61, No. 1, pp. 1-11 (cited in ISR and on p. 14 of specification).

Aydin, T.O. et al., "Temporally Coherent Local Tone Mapping of HDR Video", ACM Transactions on Graphics, Nov. 2014, vol. 33, No. 6, Article 196, pp. 196:1-196:13 (cited on p. 15 of specification).

Kuang, J. et al., "iCAM06: A refined image appearance model for HDR image rendering", Jun. 2007, J. Vis. Commun. Image R. vol. 18, pp. 406-414 (cited on p. 37 of specification).

English abstract of JP2012-143337A dated Aug. 2, 2012.

* cited by examiner

ULTRASOUND OBSERVATION DEVICE, OPERATION METHOD OF IMAGE SIGNAL PROCESSING APPARATUS, IMAGE SIGNAL PROCESSING METHOD, AND COMPUTER-READABLE RECORDING MEDIUM

CROSS REFERENCES TO RELATED APPLICATIONS

This application is a continuation of PCT international application Ser. No. PCT/JP2017/014867 filed on Apr. 11, 2017 which designates the United States, incorporated herein by reference, and which claims the benefit of priority from Japanese Patent Applications No. 2016-103532, filed on May 24, 2016, incorporated herein by reference.

BACKGROUND

1. Technical Field

The present disclosure relates to an image signal processing apparatus, an image signal processing method, and a computer-readable recording medium for performing signal processing on an input image signal.

2. Related Art

In the related art, an endoscope system has been used to observe an organ of a subject, such as a patient, in the medical field. The endoscope system includes: an endoscope that includes an insertion portion, which is provided with an imaging element at a distal end thereof and inserted into a body cavity of the subject; and a processing apparatus that is connected to a proximal end side of the insertion portion, performs image processing on an in-vivo image in accordance with an imaging signal generated by the imaging element, and displays the in-vivo image on a display unit or the like.

To observe the in-vivo image, there is a demand to observe an object with low contrast, such as redness of a gastric mucosa or a flat lesion, rather than an object with high contrast, such as a blood vessel or a mucosal structure. To cope with the demand, a technology has been disclosed, in which a highlighting process is performed on signals of predetermined color components and color difference signals between the predetermined color components of an image acquired by imaging in order to acquire an image in which an object with low contrast is highlighted (for example, see Japanese Patent No. 5159904).

SUMMARY

In some embodiments, an image signal processing apparatus includes circuitry. The circuitry includes: an imaging signal acquiring circuitry configured to after white light generated by a light source circuitry is emitted to a subject from a tip portion of an endoscope, acquire an imaging signal that is generated by an imaging element provided on the endoscope by receiving light reflected from the subject, and generate an input image signal including a base component and a detail component based on the imaging signal; a mode setting circuitry configured to change a mode to one of a first mode and a second mode for outputting the input image signal output from the imaging signal acquiring circuitry to different destinations; a dividing circuitry configured to acquire the input image signal when the mode setting circuitry sets the first mode, and divide the input image signal into a base component signal and a detail component signal; a first tone compressing circuitry configured to acquire the base component signal divided by the dividing circuitry, and perform a tone compression process on the base component signal to generate a compressed base component signal; a synthesizing circuitry configured to generate a synthetic image signal based on the detail component signal divided by the dividing circuitry and the compressed base component signal generated by the first tone compressing circuitry; and a second tone compressing circuitry configured to acquire the input image signal when the mode setting circuitry sets a second mode, and perform a tone compression process such that tone of the input image signal becomes approximately equal to tone of the compressed base component signal generated by the first tone compressing circuitry.

In some embodiments, provided is an image signal processing method. The method includes acquiring, after white light generated by a light source unit is emitted to a subject from a tip portion of an endoscope, an imaging signal including a base component and a detail component, the imaging signal that is generated by an imaging element provided on the endoscope by receiving light reflected from the subject; generating an input image signal including a base component and a detail component on the basis of the imaging signal; changing a mode to one of a first mode and a second mode for outputting the input image signal to different destinations; acquiring, by a dividing unit, the input image signal when the first mode is set, and dividing the input image signal into a base component signal and a detail component signal when a second mode different from the first mode is set; performing, by a first tone compressing unit, a tone compression process on the base component signal to generate a compressed base component signal; generating a synthetic image signal based on the detail component signal and the compressed base component signal; and acquiring, by a second tone compressing unit, the input image signal when the second mode is set, and performing a tone compression process such that tone of input image signal becomes approximately equal to tone of the compressed base component signal.

In some embodiments, provided is a non-transitory computer-readable recording medium with an executable program stored thereon. The program causes a computer to execute: acquiring, after white light generated by a light source unit is emitted to a subject from a tip portion of an endoscope, an imaging signal including a base component and a detail component, the imaging signal that is generated by an imaging element provided on the endoscope by receiving light reflected from the subject; generating an input image signal including a base component and a detail component on the basis of the imaging signal; changing a mode to one of a first mode and a second mode for outputting the input image signal to different destinations; acquiring, by a dividing unit, the input image signal when the first mode is set, and dividing the input image signal into a base component signal and a detail component signal when a second mode different from the first mode is set; performing, by a first tone compressing unit, a tone compression process on the base component signal to generate a compressed base component signal; generating a synthetic image signal based on the detail component signal and the compressed base component signal; and acquiring, by a second tone compressing unit, the input image signal when the second mode is set, and performing a tone compression process such that tone of input image signal becomes approximately equal to tone of the compressed base component signal.

The above and other features, advantages and technical and industrial significance of this disclosure will be better understood by reading the following detailed description of presently preferred embodiments of the disclosure, when considered in connection with the accompanying drawings.

DETAILED DESCRIPTION

Modes (hereinafter, referred to as "embodiments") for carrying out the present disclosure will be described below. In the embodiments, as one example of a system including an image signal processing apparatus according to the present disclosure, a medical endoscope system that captures an image inside a subject, such as a patient, and displays the image will be described. In addition, the present disclosure is not limited by the embodiments below. Furthermore, in the description of the drawings, the same components are denoted by the same reference signs.

First Embodiment

Figure 1:
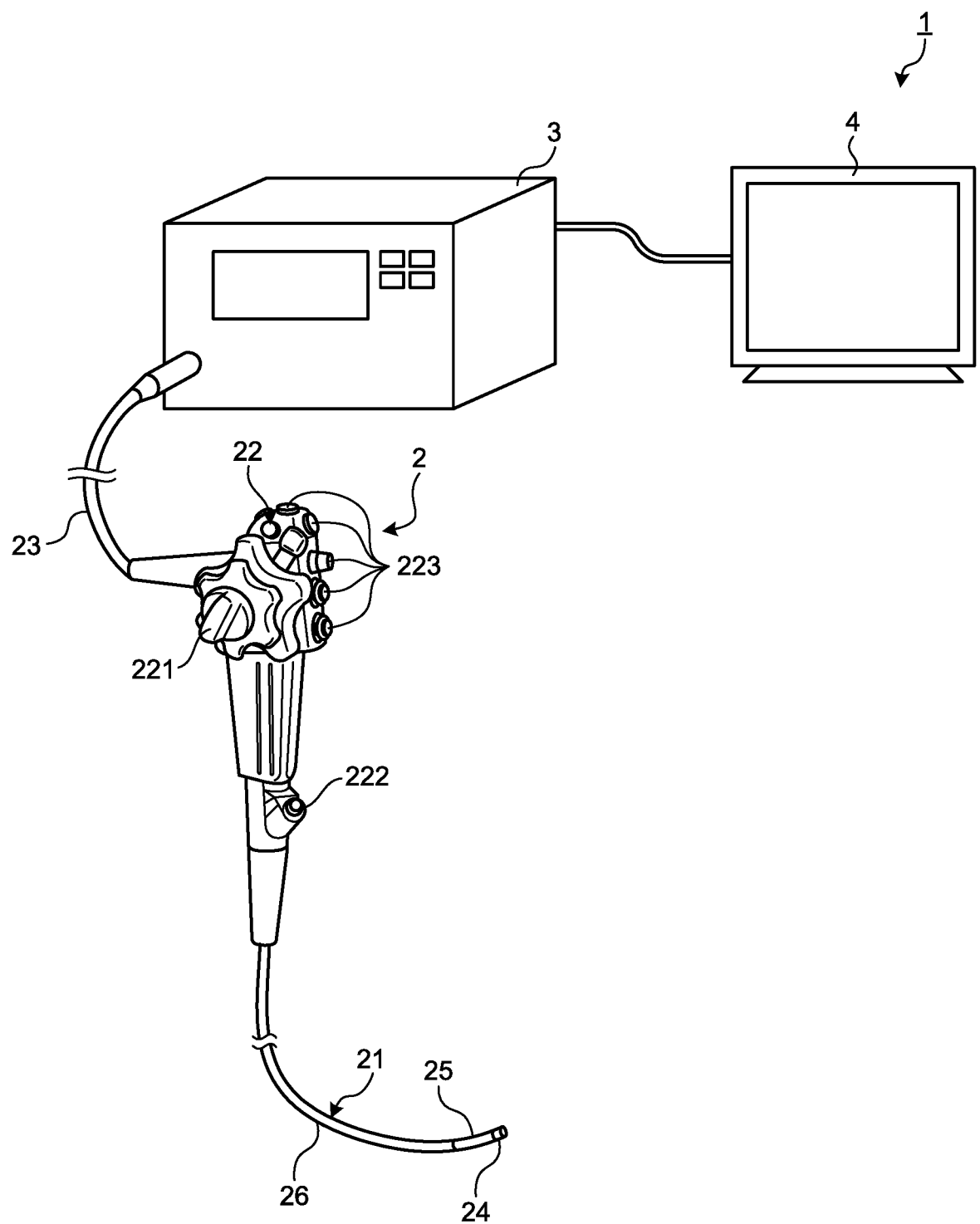
FIG. 1 is a diagram illustrating an overall configuration of an endoscope system according to a first embodiment of the present disclosure.
Figure 2:
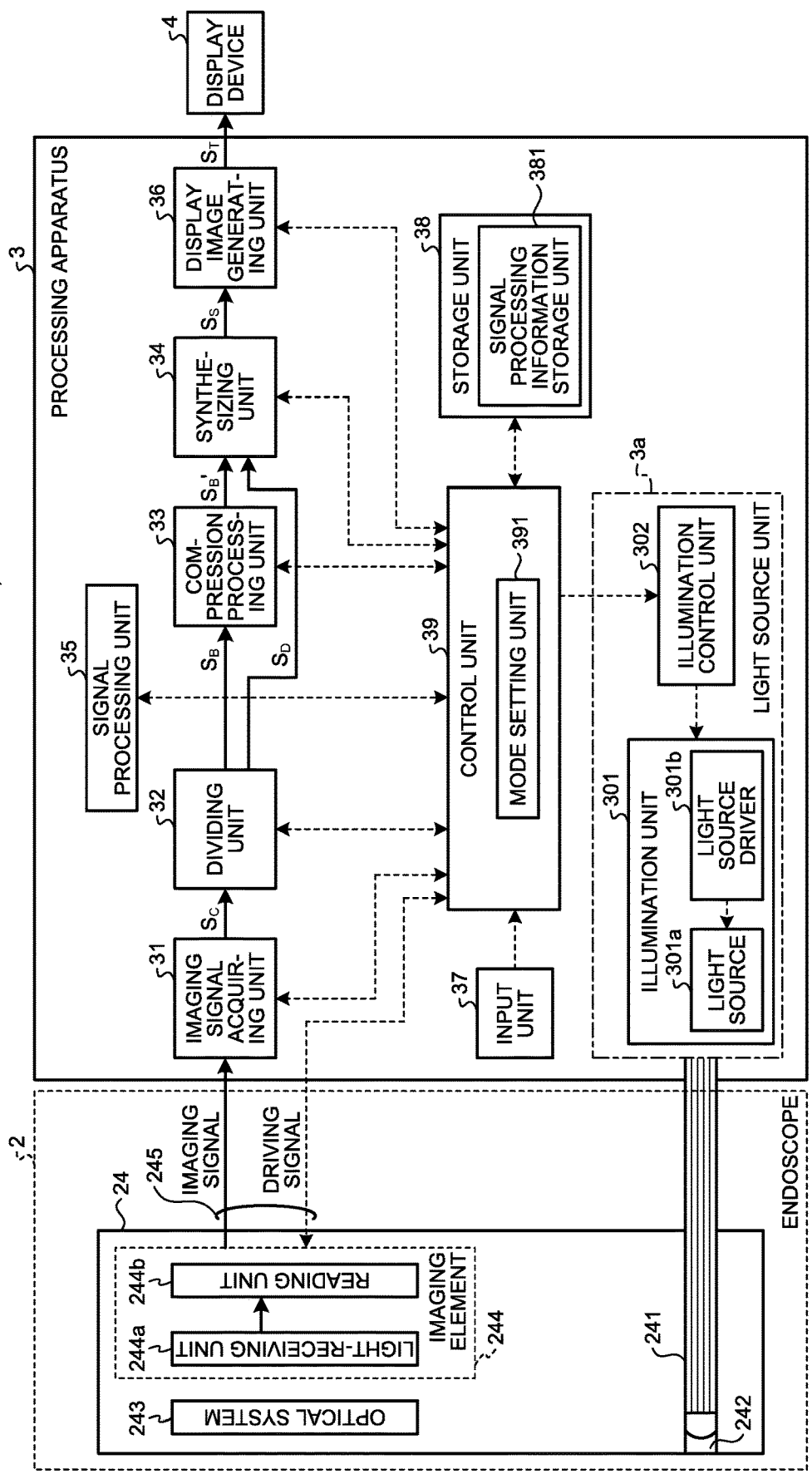
FIG. 2 is a block diagram illustrating a schematic configuration of the endoscope system according to the first embodiment of the present disclosure.
Figure 3:
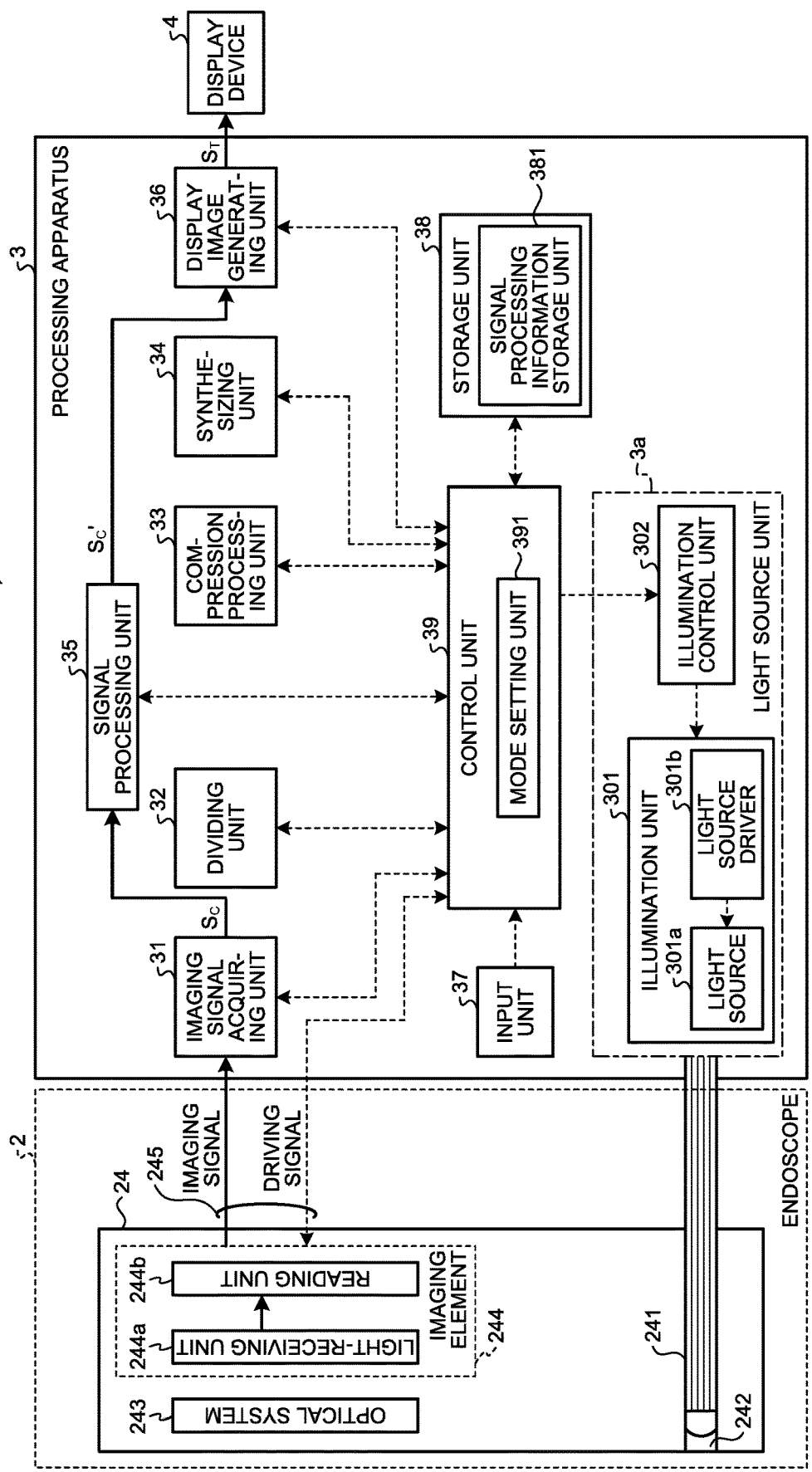
FIG. 3 is a block diagram illustrating a schematic configuration of the endoscope system according to the first embodiment of the present disclosure.

FIG. 1 is a diagram illustrating an overall configuration of an endoscope system according to a first embodiment of the present disclosure. FIGS. 2 and 3 are block diagrams illustrating schematic configurations of the endoscope system according to the first embodiment. In FIGS. 2 and 3, solid arrows indicate transfer of electrical signals related to images, and dashed arrows indicate transfer of electrical signals related to control. FIG. 2 illustrates transfer of signals in a highlighted compression mode to be described later. FIG. 3 illustrates transfer of signals in a normal mode to be described later.

An endoscope system 1 illustrated in FIG. 1 and FIG. 2 includes: an endoscope 2 that captures an in-vivo image of a subject by introducing a tip portion into the subject; a processing apparatus 3 that includes a light source unit 3a for generating illumination light to be emitted from a distal end of the endoscope 2 and that performs predetermined signal processing on an imaging signal captured by the endoscope 2 and comprehensively controls operation of the entire endoscope system 1; and a display device 4 that displays an in-vivo image generated through the signal processing performed by the processing apparatus 3.

The endoscope 2 includes a flexible insertion portion 21 that has a long and thin shape, an operating unit 22 that is connected to a proximal end side of the insertion portion 21 and receives input of various operation signals, and a universal cord 23 that extends from the operating unit 22 in a direction different from a direction in which the insertion portion 21 extends and that houses various cables connected to the processing apparatus 3 (including the light source unit 3a).

The insertion portion 21 includes a tip portion 24 provided with a built-in imaging element 244 including pixels that are arranged two-dimensionally and that receive light and generate signals by performing photoelectric conversion on the light, a bending portion 25 that is constituted of a plurality of bending pieces and is freely bendable, and a flexible tube portion 26 that is connected to a proximal end side of the bending portion 25 and that has an elongated shape. The insertion portion 21 is introduced into a body cavity of the subject, and captures an image of an object, such as body tissue, at a position where external light does not reach, by using the imaging element 244.

The tip portion 24 includes a light guide 241 that is constituted by fiberglass or the like and serves as a light guide of light emitted by the light source unit 3a, an illumination lens 242 that is provided at a distal end of the light guide 241, an optical system 243 for collecting light, and the imaging element 244 that is provided at an image forming position of the optical system 243, that receives light collected by the optical system 243, performs photoelectric conversion to obtain an electrical signal, and performs predetermined signal processing.

The optical system 243 is constituted by one or more lenses and has an optical zoom function to change an angle of view and a focus function to change a focal point.

The imaging element 244 performs photoelectric conversion on light received from the optical system 243 and generates an electrical signal (imaging signal). Specifically, the imaging element 244 includes: a light-receiving unit 244a provided with a plurality of pixels, which are arranged in an matrix manner, which have respective photodiodes for accumulating charges corresponding to amounts of light received and respective capacitors for converting charges transferred from the photodiodes into voltage levels, and which perform photoelectric conversion on light received from the optical system 243 to generate electrical signals; and a reading unit 244b that sequentially reads the electrical signals generated by arbitrary pixels that are set as read targets among the plurality of pixels of the light-receiving unit 244a and outputs the read signals as imaging signals. The light-receiving unit 244a is provided with a color filter, and each of the pixels receives light of any of wavelength bands of color components of red (R), green (G), and blue (B). The imaging element 244 controls various kinds of operation of the tip portion 24 in accordance with a driving signal received from the processing apparatus 3. The imaging element 244 is realized using a charge coupled device (CCD) image sensor or a complementary metal oxide semiconductor (CMOS) image sensor, for example.

The operating unit 22 includes a bending knob 221 for causing the bending portion 25 to bend in a vertical direction and a horizontal direction, a treatment tool insertion portion 222 for inserting a treatment tool, such as a biopsy forceps, an electric scalpel, or an inspection probe, into the subject, and a plurality of switches 223 as an operation input unit for receiving input of operation instruction signals for the processing apparatus 3 and peripheral devices, such as an air supply means, a water supply means, and screen display control. The treatment tool inserted from the treatment tool insertion portion 222 comes out from an opening portion (not illustrated) via a treatment tool channel (not illustrated) of the tip portion 24.

The universal cord 23 houses at least the light guide 241 and an assembly cable 245 in which one or more signal lines are bundled. The assembly cable 245 includes a signal line for transferring an imaging signal, a signal line for transferring a driving signal for driving the imaging element 244, and a signal line for transmitting and receiving information including unique information on the endoscope 2 (the imaging element 244) or the like. In the present embodiment, an explanation will be given based on the assumption that electrical signals are transferred using the signal lines; however, it may be possible to transfer optical signals or transfer signals between the endoscope 2 and the processing apparatus 3 using wireless communication.

Next, a configuration of the processing apparatus 3 will be described. The processing apparatus 3 includes an imaging signal acquiring unit 31, a dividing unit 32, a compression processing unit 33, a synthesizing unit 34, a signal processing unit 35, a display image generating unit 36, an input unit 37, a storage unit 38, and a control unit 39. The image signal processing apparatus according to the present disclosure is constituted by at least the dividing unit 32, the compression processing unit 33, and the synthesizing unit 34.

The imaging signal acquiring unit 31 receives, from the endoscope 2, an imaging signal output by the imaging element 244. The imaging signal acquiring unit 31 performs signal processing, such as noise removal, analog-to-digital (A/D) conversion, and a synchronization process (which is performed when an imaging signal for each of the color components is obtained using a color filter or the like, for example) on the acquired imaging signal. The imaging signal acquiring unit 31 generates an input image signal $S_C$ that includes an input image to which RGB color components are added through the signal processing as described above. The imaging signal acquiring unit 31 inputs the generated input image signal $S_C$ to the dividing unit 32 and inputs and stores the generated input image signal $S_C$ in the storage unit 38. The imaging signal acquiring unit 31 is constituted by a general-purpose processor, such as a central processing unit (CPU), or a dedicated processor, such as various arithmetic circuits or the like that implement specific functions, in particular, such as an application specific integrated circuit (ASIC) or a field programmable gate array (FPGA) that is a programmable logic device in which processing contents are rewritable.

As illustrated in FIG. 2, the dividing unit 32 acquires the input image signal $S_C$ from the imaging signal acquiring unit 31, and divides an image component into a visually weakly correlated component and a visually strongly correlated component. The image component described herein is a component for generating an image and a component constituted of a base component and/or a detail component to be described later. The dividing process may be performed using a technology (Retinex theory) described in, for example, Lightness and retinex theory, E. H. Land, J. J. McCann, Journal of the Optical Society of America, 61 (1), 1-11 (1971). In the dividing process based on the Retinex theory, the visually weakly correlated component is a component corresponding to an illumination light component of an object. The visually weakly correlated component is generally called as a base component. In contrast, the visually strongly correlated component is a component corresponding to a reflectance component of an object. The visually strongly correlated component is generally called as a detail component. The detail component is a component obtained by dividing a signal constituting an image by the base component. The detail component includes a contour (edge) component and a contrast component, such as a texture component, of an object. The dividing unit 32 inputs a signal (hereinafter, referred to as a "base component signal $S_B$") that includes the base component as a component signal to the compression processing unit 33, and a signal (hereinafter, referred to as a "detail component signal $S_D$") that includes the detail component as a component signal to the synthesizing unit 34. Meanwhile, when an input image signal of each of the RGB color components is input, the dividing unit 32 performs the dividing process on each of the color component signals. In signal processing described hereinafter, the same processing is performed on each of the color components.

The component dividing process performed by the dividing unit 32 may be performed using an Edge-aware filtering technology described in, for example, Temporally Coherent Local Tone Mapping of HDR Video, T. O. Aydin, et al., ACM Transactions on Graphics, Vol 33, November 2014. Further, the dividing unit 32 may divide a spatial frequency into a plurality of frequency bands. The dividing unit 32 is constituted by a general-purpose processor, such as a CPU, or a dedicated processor, such as various arithmetic circuits that implement specific functions, in particular, such as an ASIC or an FPGA.

The compression processing unit 33 performs a compression process on the base component signal $S_B$ among the component signals divided by the dividing unit 32. Specifically, the compression processing unit 33 performs a well-known tone compression process, such as a non-linear process, on the base component signal $S_B$. The compression processing unit 33 performs the tone compression process using the same parameter as a parameter that is used in a tone compression process performed by the signal processing unit 35 to be described later. Here, the "same" parameter includes not only an identical value but also values that are a few percent larger or smaller than the identical value. The compression processing unit 33 inputs a base component signal $S_B'$ that is generated through the tone compression process to the synthesizing unit 34. The compression processing unit 33 is constituted by a general-purpose processor, such as a CPU, or a dedicated processor, such as various arithmetic circuits that implement specific functions, in particular, such as an ASIC or an FPGA.

The synthesizing unit 34 synthesizes the detail component signal $S_D$ divided by the dividing unit 32 and the base component signal $S_B'$ subjected to the tone compression process by the compression processing unit 33. The synthesizing unit 34 generates a synthetic image signal $S_S$ by synthesizing the base component signal $S_B'$ and the detail component signal $S_D$. The synthesizing unit 34 inputs the generated synthetic image signal $S_S$ to the display image generating unit 36. The synthesizing unit 34 is constituted by a general-purpose processor, such as a CPU, or a dedicated processor, such as various arithmetic circuits that implement specific functions, in particular, such as an ASIC or an FPGA.

As illustrated in FIG. 3, the signal processing unit 35 acquires the input image signal $S_C$ from the imaging signal acquiring unit 31, and performs well-known image processing, such as a tone compression process, on a signal of each of the color components. The signal processing unit 35 performs the tone compression process on the signal of each of the color components through a non-linear process using a function that is stored in the storage unit 38. The signal processing unit 35 may perform the tone compression process through a linear process, or may set a plurality of functions in advance such that any of the functions is selectable via the input unit 37. The function used in this case uses a luminance value of the input image signal $S_C$ as an input value, and outputs a compressed luminance value corresponding to the input luminance value. With this operation, an input image signal $S_C'$ for which white balance is adjusted and tone is corrected is generated. The signal processing unit 35 inputs the generated input image signal $S_C'$ to the display image generating unit 36. The signal processing unit 35 is constituted by a general-purpose processor, such as a CPU, or a dedicated processor, such as various arithmetic circuits that implement specific functions, in particular, such as an ASIC or an FPGA.

The display image generating unit 36 generates an image signal $S_T$ for display by performing a process on the synthetic image signal $S_S$ or the input image signal $S_C'$ so as to obtain a signal in a certain mode that can be displayed on the display device 4. For example, a synthetic image signal of each of the RGB color components is assigned to each of RGB channels. The display image generating unit 36 outputs the generated image signal $S_T$ to the display device 4.

The input unit 37 is realized using a keyboard, a mouse, a switch, or a touch panel, and receives input of various signals, such as an operation instruction signal for giving an instruction on operation of the endoscope system 1. The input unit 37 may include a switch provided on the operating unit 22 or a portable terminal, such as an external tablet computer.

The storage unit 38 stores therein various programs for operating the endoscope system 1, and data including various parameters or the like needed for operation of the endoscope system 1. Further, the storage unit 38 stores therein identification information on the processing apparatus 3. Here, the identification information includes unique information (ID), a model year, specifications information, and the like on the processing apparatus 3.

The storage unit 38 includes a signal processing information storage unit 381 that stores therein signal processing information, such as a function, that is used when the compression processing unit 33 performs the tone compression process.

Further, the storage unit 38 stores therein various programs including an image signal processing program for implementing an image signal processing method of the processing apparatus 3. The various programs may be widely distributed by being recorded in a computer readable recording medium, such as a hard disk, a flash memory, a compact disc read only memory (CD-ROM), a digital versatile disk-ROM (DVD-ROM), or a flexible disk. The various programs as described above may be acquired by downloading via a communication network. The communication network described herein is realized by, for example, an existing public line network, a local area network (LAN), or a wide area network (WAN), regardless of whether it is wired or wireless.

The storage unit 38 having the configuration as described above is realized using a ROM in which the various programs and the like are installed in advance, a random access memory (RAM) for storing arithmetic parameters for each process, data, and the like, or a hard disk.

The control unit 39 controls drive of each of components including the imaging element 244 and the light source unit 3a, and controls input and output of information with respect to each of the components. The control unit 39 refers to control information data (for example, a read timing or the like), which is stored in the storage unit 38 and which is for controlling imaging, and transmits the data as a driving signal to the imaging element 244 via a predetermined signal line included in the assembly cable 245. The control unit 39 reads a function stored in the signal processing information storage unit 381, and inputs the function to the compression processing unit 33 to perform the tone compression process. The control unit 39 is constituted by a general-purpose processor, such as a CPU, or a dedicated processor, such as various arithmetic circuits that implement specific functions, in particular, such as an ASIC or an FPGA.

Further, the control unit 39 includes a mode setting unit 391 that sets a mode. The mode setting unit 391 sets any of a normal mode, in which an image is generated through normal signal processing that is based on an imaging signal, and a highlighted compression mode, in which a compression process is performed only on the base component signal $S_B$ divided by the dividing unit 32 to generate an image in which the detail component is highlighted. The mode setting unit 391 sets a mode based on, for example, an instruction signal received via the input unit 37. The control unit 39 causes each of the blocks to perform signal processing corresponding to the mode set by the mode setting unit 391. While the explanation is given based on the assumption that the mode setting unit 391 is provided in the control unit 39, the mode setting unit 391 may be provided separately from the control unit 39.

Next, a configuration of the light source unit 3a will be described. The light source unit 3a includes an illumination unit 301 and an illumination control unit 302. The illumination unit 301 sequentially emits illumination light of different exposure amounts in a switching manner to an object (subject) under the control of the illumination control unit 302. The illumination unit 301 includes a light source 301a and a light source driver 301b.

The light source 301a is constituted by a light emitting diode (LED) light source that emits white light, one or more lenses, and the like, and emits light (illumination light) by the drive of the LED light source. The illumination light generated by the light source 301a is emitted toward the subject from a distal end of the tip portion 24 via the light guide 241. The light source 301a may be constituted by a red LED light source, a green LED light source, and a blue LED light source and emit illumination light. Further, the light source 301a may use a laser light source or a lamp, such as a xenon lamp or a halogen lamp.

The light source driver 301b supplies electrical current to the light source 301a to cause the light source 301a to emit illumination light, under the control of the illumination control unit 302.

The illumination control unit 302 controls an amount of electricity to be supplied to the light source 301a on the basis of a control signal from the control unit 39, and controls a driving timing of the light source 301a.

The display device 4 displays a display image corresponding to the image signal $S_T$ generated by the processing apparatus 3 (the display image generating unit 36) via a video cable. The display device 4 is constituted by a monitor made of liquid crystal, organic electro luminescence (EL), or the like.

In the endoscope system 1 described above, when the mode setting unit 391 sets the highlighted compression mode, the dividing unit 32 divides a component included in the imaging signal into two component signals on the basis of an imaging signal input to the processing apparatus 3, the compression processing unit 33 performs the tone compression process on the base component signal $S_B$ among the divided component signals, the synthesizing unit 34 synthesizes the component signal subjected to the compression process and the detail component signal $S_D$, the display image generating unit 36 generates the image signal $S_T$ subjected to signal processing for display on the basis of the synthesized signal, and the display device 4 displays a display image based on the image signal $S_T$.

Figure 4:
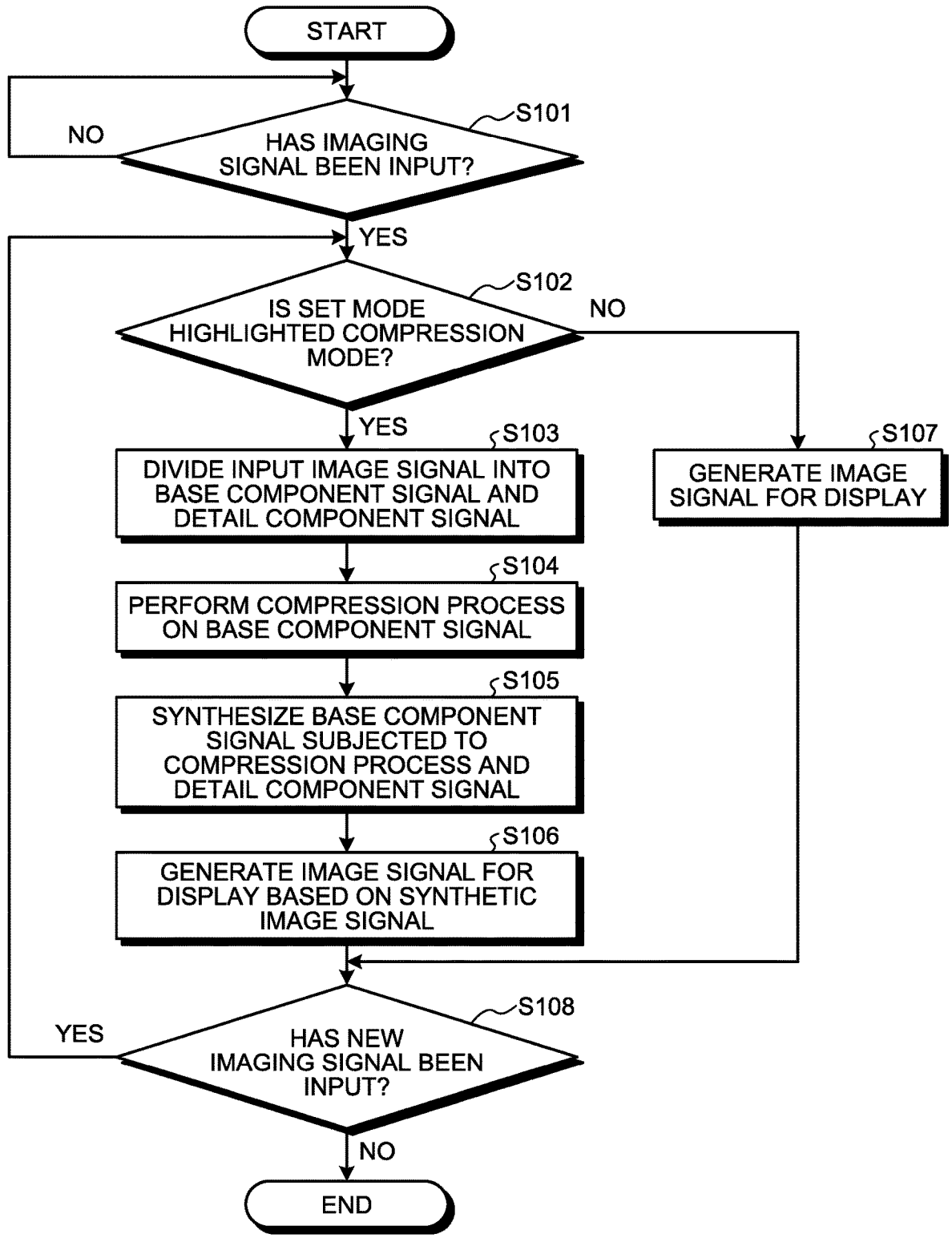
FIG. 4 is a flowchart illustrating an image signal processing method performed by a processing apparatus according to the first embodiment of the present disclosure.

FIG. 4 is a flowchart illustrating the image signal processing method performed by the processing apparatus according to the first embodiment of the present disclosure. In the following description, it is assumed that each of the units operates under the control of the control unit 39.

If the imaging signal acquiring unit 31 of the control unit 39 has acquired an imaging signal from the endoscope 2 (Step S101: Yes), the process proceeds to Step S102. In contrast, if the imaging signal acquiring unit 31 has not received input of an imaging signal from the endoscope 2 (Step S101: No), the control unit 39 repeatedly checks input of an imaging signal.

At Step S102, the control unit 39 determines whether a set mode is the highlighted compression mode. If the control unit 39 determines that the set mode is not the highlighted compression mode, that is, if the control unit 39 determines that the set mode is the normal mode (Step S102: No), the process proceeds to Step S107. In contrast, if the control unit 39 determines that the set mode is the highlighted compression mode (Step S102: Yes), the control unit 39 inputs the input image signal $S_C$ generated by the imaging signal acquiring unit 31 to the dividing unit 32, and the process proceeds to Step S103.

At Step S103, the dividing unit 32 divides the input image signal $S_C$ into the detail component signal $S_D$ and the base component signal $S_B$ (dividing step). The dividing unit 32 inputs the base component signal $S_B$ generated through the above-described dividing process to the compression processing unit 33, and inputs the detail component signal $S_D$ to the synthesizing unit 34.

Figure 5:
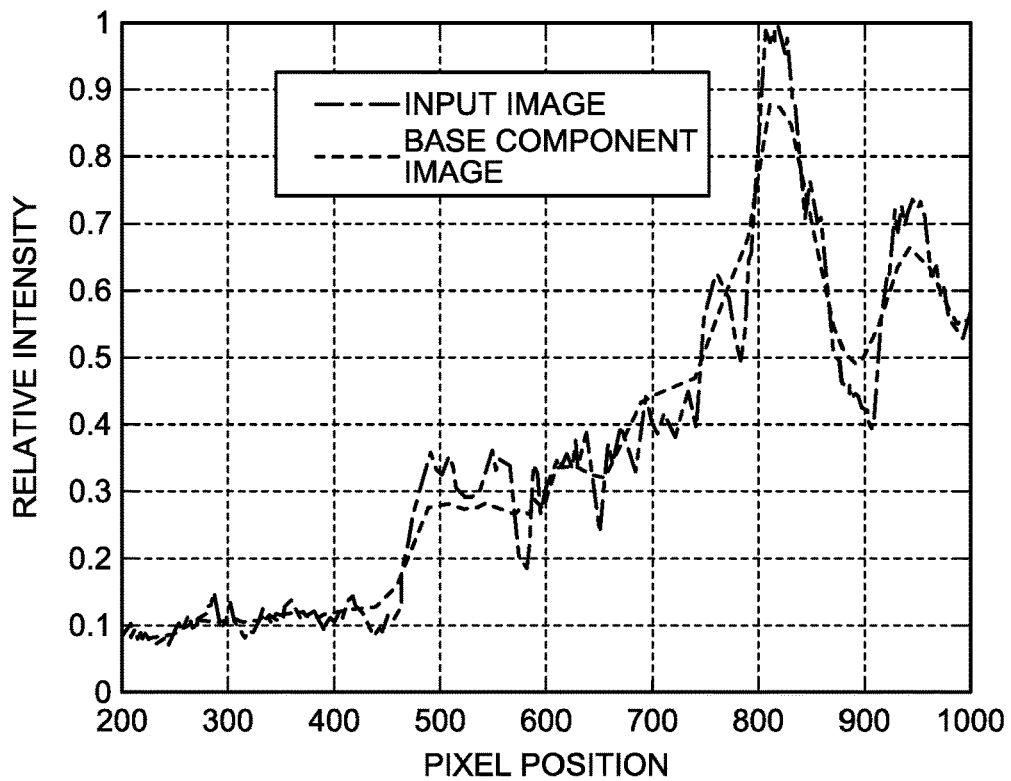
FIG. 5 is a diagram for explaining an image signal processing method performed by the endoscope system according to the first embodiment of the present disclosure, and is a diagram illustrating a relative intensity of each of an input image and a base component image at each of pixel positions on a certain pixel line.
Figure 6:
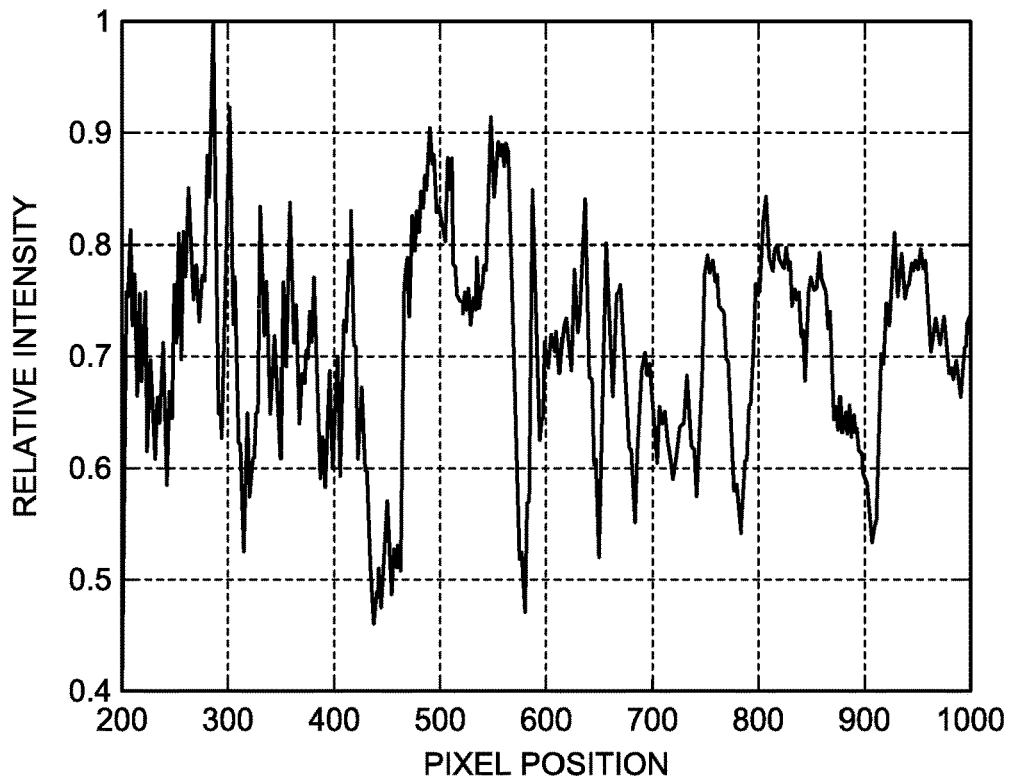
FIG. 6 is a diagram for explaining the image signal processing method performed by the endoscope system according to the first embodiment of the present disclosure, and is a diagram illustrating a relative intensity of a detail component image at each of pixel positions on a certain pixel line.

FIG. 5 is a diagram for explaining the image signal processing method performed by the endoscope system according to the first embodiment of the present disclosure, and is a diagram illustrating a relative intensity of each of an input image and a base component image at each of pixel positions on a certain pixel line. FIG. 6 is a diagram for explaining the image signal processing method performed by the endoscope system according to the first embodiment of the present disclosure, and is a diagram illustrating a relative intensity of a detail component image at each of pixel positions on a certain pixel line. The input image is an image corresponding to the input image signal $S_C$, and the base component image is an image corresponding to the base component signal $S_B$. The pixel lines illustrated in FIGS. 5 and 6 are the same pixel line, and relative intensities at positions of a $200^{th}$ pixel to a $1000^{th}$ pixel on the pixel line are illustrated. FIG. 5 illustrates an example in which the maximum value of luminance values of the input image is normalized to one. FIG. 6 illustrates an example in which the maximum value of luminance values of the detail component image is normalized to one.

As illustrated in FIG. 5, it can be seen that a low frequency component is extracted as the base component from a change in the luminance of the input image. This corresponds to the visually weakly correlated component. In contrast, the detail component is a component obtained by removing the base component from the change in the luminance of the input image, and is a component that includes a large amount of reflectance components (see FIG. 6). This corresponds to the visually strongly correlated component.

Thereafter, the compression processing unit 33 performs the tone compression process on the base component signal $S_B$ among the component signals divided by the dividing unit 32 (Step S104: compression processing step). In the tone compression process at this time, the same parameter as a parameter used in the tone compression process that is performed by the signal processing unit 35 in the normal mode. The compression processing unit 33 inputs the base component signal $S_B'$ subjected to the tone compression process to the synthesizing unit 34.

When the detail component signal $S_D$ is input from the dividing unit 32 and the base component signal $S_B'$ subjected to the tone compression process is input from the compression processing unit 33, the synthesizing unit 34 generates the synthetic image signal $S_S$ by synthesizing the base component signal $S_B'$ and the detail component signal $S_D$ (Step S105: synthesizing step). The synthesizing unit 34 inputs the generated synthetic image signal $S_S$ to the display image generating unit 36.

When the synthetic image signal $S_S$ is input from the synthesizing unit 34, the display image generating unit 36 generates the image signal $S_T$ for display by performing a process on the synthetic image signal $S_S$ so as to obtain a signal in a certain mode that can be displayed on the display device 4 (Step S106). The display image generating unit 36 outputs the generated image signal $S_T$ to the display device 4. The display device 4 displays an image corresponding to the input image signal $S_T$.

Further, at Step S107 following Step S102, the control unit 39 generates the image signal $S_T$ for display, on the basis of the imaging signal. Specifically, the signal processing unit 35 generates the input image signal $S_C'$ by performing image processing, such as a tone compression process, on the input image signal $S_C$ (signal processing step). Thereafter, the display image generating unit 36 generates the image signal $S_T$ for display by performing a process on the input image signal $S_C'$ generated by the signal processing unit 35 so as to obtain a signal in a certain mode that can be displayed on the display device 4. The display image generating unit 36 outputs the generated image signal $S_T$ to the display device 4. The display device 4 displays an image corresponding to the input image signal $S_T$.

After the display image generating unit 36 has generated the image signal $S_T$, the control unit 39 determines whether a new imaging signal has been input (Step S108). For example, the control unit 39 determines whether the imaging signal acquiring unit 31 has received input of a new imaging signal. If the control unit 39 determines that a new imaging signal has not been input (Step S108: No), the image signal processing ends.

If the control unit 39 determines that a new imaging signal has been input (Step S108: Yes), the process returns to Step S102, and the control unit 39 performs the image signal generation process for the new imaging signal.

According to the first embodiment of the present disclosure as described above, when the mode setting unit 391 sets the highlighted compression mode, the dividing unit 32 acquires the input image signal $S_C$ from the imaging signal acquiring unit 31 and divides the input image signal into the base component signal $S_B$ and a component signal other than the base component signal $S_B$, in particular, the detail component signal $S_D$ including a contrast component, and the compression processing unit 33 performs the tone compression process on the base component signal $S_B$. In this case, the parameter used in the tone compression process performed by the compression processing unit 33 is set to be identical to the parameter used in the tone compression process that is performed by the signal processing unit 35 in the normal mode. By causing the compression processing unit 33 to perform the tone compression process using the same parameter as that of the tone compression process performed by the signal processing unit 35, it is possible to compress tone while maintaining colors of a normal image; therefore, even when the tone compression is performed, it is possible to prevent a change in the colors. Further, the compression processing unit 33 performs the tone compression process on only the base component, and an image is generated by synthesizing the detail component including the contrast component without any change; therefore, the contrast component is not compressed through the tone compression process, so that it is possible to generate an image with good visibility.

Second Embodiment

Figure 7:
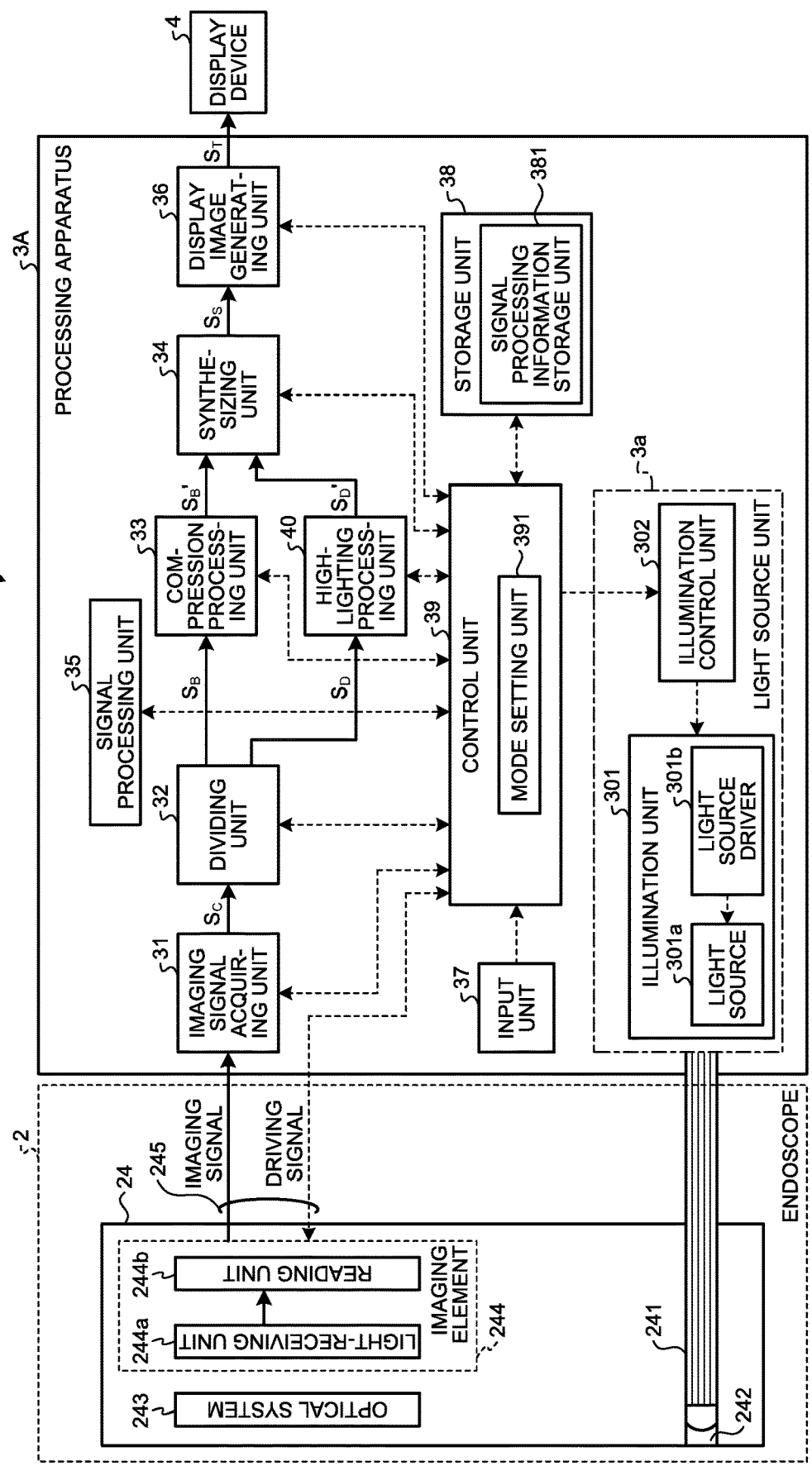
FIG. 7 is a block diagram illustrating a schematic configuration of an endoscope system according to a second embodiment of the present disclosure.

In a second embodiment, a highlighting process is performed on the detail component signal in addition to performing the tone compression process on the base component signal $S_B$ as described above. FIG. 7 is a block diagram illustrating a schematic configuration of an endoscope system according to the second embodiment. The same components as those of the endoscope system 1 according to the first embodiment as described above are denoted by the same reference signs. In FIG. 7, solid arrows indicate transfer of electrical signals related to images, and dashed arrows indicate transfer of electrical signals related to control. FIG. 7 illustrates transfer of electrical signals in the highlighted compression mode.

An endoscope system 1A according to the second embodiment includes a processing apparatus 3A instead of the processing apparatus 3 in the configuration of the endoscope system 1 according to the first embodiment as described above. The processing apparatus 3A includes a highlighting processing unit 40 in addition to the components of the processing apparatus 3 according to the first embodiment as described above. In the second embodiment, the dividing unit 32 inputs the divided detail component signal $S_D$ to the highlighting processing unit 40.

The highlighting processing unit 40 performs a highlighting process on the detail component signal $S_D$ among the component signals divided by the dividing unit 32. The highlighting processing unit 40 acquires a function that is set in advance by referring to the storage unit 38, and performs a gain-up process of increasing a signal value of each of color components at each of pixel positions based on the acquired function. Specifically, assuming that a signal value of the red color component is denoted by $R_{Detail}$, a signal value of the green color component is denoted by $G_{Detail}$, and a signal value of the blue color component is denoted by $B_{Detail}$ among color component signals included in the detail component signal $S_D$, the highlighting processing unit 40 calculates signal values of the respective color components as $R_{Detail}{}^{\alpha}$, $G_{Detail}{}^{\beta}$, and $B_{Detail}{}^{\gamma}$. Here, in the second embodiment, α, β, and γ are parameters that are set in advance. For example, a function f(L) of luminance is set for each of the parameters α, β, and γ, and the parameters α, β, and γ are calculated in accordance with an input luminance value L. The function f(L) may be a linear function or an exponential function. The highlighting processing unit 40 inputs the detail component signal $S_D'$ subjected to the highlighting process to the synthesizing unit 34. The highlighting processing unit 40 is constituted by a general-purpose processor, such as a CPU, or a dedicated processor, such as various arithmetic circuits that implement specific functions, in particular, such as an ASIC or an FPGA.

Meanwhile, the parameters α, β, and γ may be set to the same value or arbitrary different values. The parameters α, β, and γ are set via the input unit 37, for example.

In the second embodiment, the synthesizing unit 34 synthesizes the detail component signal $S_D'$ subjected to the highlighting process by the highlighting processing unit 40 and the base component signal $S_B'$ subjected to the tone compression process by the compression processing unit 33. The synthesizing unit 34 inputs the generated synthetic image signal $S_S$ to the display image generating unit 36.

Figure 8:
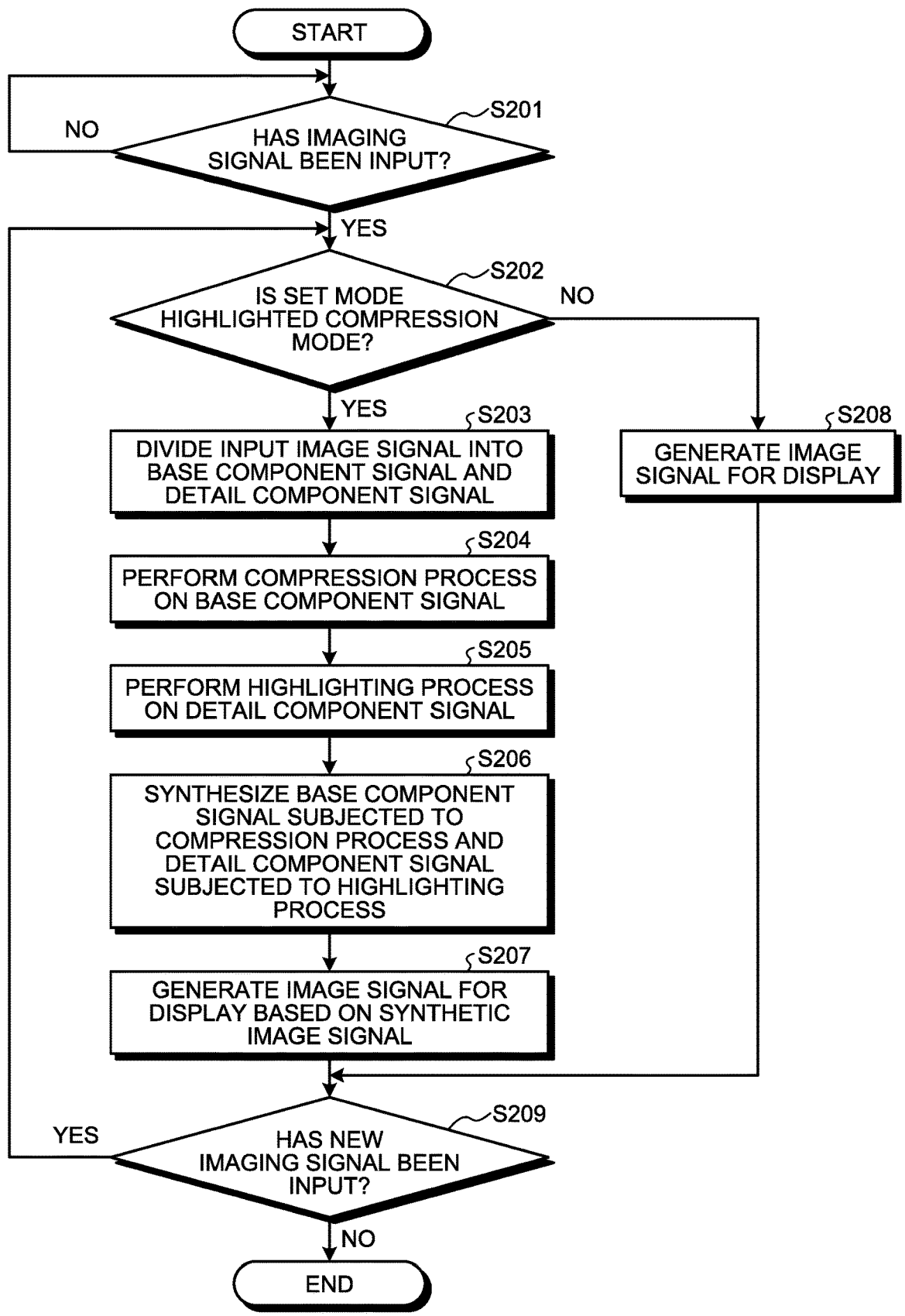
FIG. 8 is a flowchart illustrating an image signal processing method performed by a processing apparatus according to the second embodiment of the present disclosure.

FIG. 8 is a flowchart illustrating an image signal processing method performed by the processing apparatus according to the second embodiment of the present disclosure. In the following description, it is assumed that each of the units operates under the control of the control unit 39.

If the imaging signal acquiring unit 31 of the control unit 39 has acquired an imaging signal from the endoscope 2 (Step S201: Yes), the process proceeds to Step S202. In contrast, if the imaging signal acquiring unit 31 has not received input of an imaging signal from the endoscope 2 (Step S201: No), the control unit 39 repeatedly checks input of an imaging signal.

At Step S202, the control unit 39 determines whether a set mode is the highlighted compression mode. If the control unit 39 determines that the set mode is not the highlighted compression mode, that is, if the control unit 39 determines that the set mode is the normal mode (Step S202: No), the process proceeds to Step S208. In contrast, if the control unit 39 determines that the set mode is the highlighted compression mode (Step S202: Yes), the control unit 39 inputs the input image signal $S_C$ generated by the imaging signal acquiring unit 31 to the dividing unit 32, and the process proceeds to Step S203.

At Step S203, when the input image signal $S_C$ is input, the dividing unit 32 divides the input image signal $S_C$ into a detail component signal and a base component signal (dividing step). The dividing unit 32 inputs the detail component signal $S_D$ generated through the above-described dividing process to the highlighting processing unit 40, and inputs the base component signal $S_B$ to the compression processing unit 33.

Thereafter, the compression processing unit 33 performs a compression process on the base component signal $S_B$ (Step S204: compression processing step). The compression processing unit 33 inputs the base component signal $S_B'$ subjected to the compression process to the synthesizing unit 34.

After the compression processing unit 33 has performed the tone compression process, the highlighting processing unit 40 performs the highlighting process on the input detail component signal $S_D$ (Step S205). The highlighting processing unit 40 inputs the detail component signal $S_D'$ subjected to the highlighting process to the synthesizing unit 34. As for Step S204 and Step S205, it may be possible to first perform Step S205 or perform both of the steps simultaneously.

When the detail component signal $S_D'$ subjected to the highlighting process is input from the highlighting processing unit 40 and the base component signal $S_B'$ subjected to the tone compression is input from the compression processing unit 33, the synthesizing unit 34 generates the synthetic image signal $S_S$ by synthesizing the base component signal $S_B'$ and the detail component signal $S_D'$ (Step S206: synthesizing step). The synthesizing unit 34 inputs the generated synthetic image signal $S_S$ to the display image generating unit 36.

When the synthetic image signal $S_S$ is input from the synthesizing unit 34, the display image generating unit 36 generates the image signal $S_T$ for display by performing signal processing on the synthetic image signal $S_S$ so as to obtain a signal in a certain mode that can be displayed on the display device 4 (Step S207). The display image generating unit 36 outputs the generated image signal $S_T$ to the display device 4. The display device 4 displays an image corresponding to the input image signal $S_T$.

Further, at Step S208 following Step S202, the control unit 39 generates the image signal $S_T$ for display, on the basis of the imaging signal. Specifically, the signal processing unit 35 generates the input image signal $S_C'$ by performing image processing, such as the tone compression process, on the input image signal $S_C$. Thereafter, the display image generating unit 36 generates the image signal $S_T$ for display by performing a process on the input image signal $S_C'$ generated by the signal processing unit 35 so as to obtain a signal in a certain mode that can be displayed on the display device 4. The display image generating unit 36 outputs the generated image signal $S_T$ to the display device 4. The display device 4 displays an image corresponding to the input image signal $S_T$.

After the display image generating unit 36 has generated the image signal $S_T$, the control unit 39 determines whether a new imaging signal has been input (Step S209). For example, the control unit 39 determines whether the imaging signal acquiring unit 31 has received input of a new imaging signal. If the control unit 39 determines that a new imaging signal has not been input (Step S209: No), the image signal processing ends.

If the control unit 39 determines that a new imaging signal has been input (Step S209: Yes), the process returns to Step S202, and the control unit 39 performs the image signal generation process for the new imaging signal.

According to the second embodiment of the present disclosure as described above, it is possible to achieve the same effect as that of the first embodiment as described above, and, because the highlighting processing unit 40 performs the highlighting process on the detail component signal $S_D$, a visually strongly correlated component included in the detail component signal is intensified, so that it becomes possible to generate an image with good visibility, in which an object with low contrast is intensified.

Meanwhile, in the second embodiment as described above, it may be possible to cause the highlighting processing unit 40 to perform the highlighting process on the base component signal $S_B$. In this case, the highlighting processing unit 40 performs the highlighting process such that the intensity of highlight of the base component signal $S_B$ becomes lower than the intensity of highlight of the detail component signal $S_D$.

Furthermore, in the second embodiment as described above, the explanation has been described in which the highlighting processing unit 40 performs the highlighting process on the detail component signal $S_D$ using the parameters α, β, and γ that are set in advance. However, it may be possible to set values of α, β, and γ depending on an area corresponding to the base component, a type of a lesion, an observation mode, an observation region, an observation depth, a structure, or the like, and adaptively perform the highlighting process. Examples of the observation mode include a normal observation mode for acquiring an imaging signal by emitting normal white light, and a special light observation mode for acquiring an imaging signal by emitting special light.

Moreover, it may be possible to determine the values of the parameters α, β, and γ depending on a luminance value of a predetermined pixel region (an average value, a mode value, or the like). In images obtained by imaging, a brightness adjustment amount (gain map) changes for each image, and a gain coefficient is different depending on a pixel position even with the same luminance value. As an index to adaptively perform adjustment with respect to a difference in the adjustment amount as described above, a technique described in, for example, iCAM06: A refined image appearance model for HDR image rendering, Jiangtao Kuang, et al, J. Vis. Commun. Image R, 18(2007) 406-414 has been known. Specifically, an adjustment equation is set for each of the color components by raising an exponential part (F+0.8) of $S_D'=S_D^{(F+0.8)}$, which is an adjustment equation of a detail component signal described in the above-described document, to the power of α', β', or γ', which is a parameter determined for each of the color components. For example, the adjustment equation for the red color component is $S_D'=S_D^{(F+0.8)[<]BEGINITALmα'}$. The highlighting processing unit 40 performs the highlighting process on the detail component signal using the adjustment equation set for each of the color components. Meanwhile, F in the equation is a function based on an image appropriate for a low frequency band at each of the pixel positions, that is, a function based on a spatial change.

In the first and second embodiments as described above, it has been explained that the imaging signal acquiring unit 31 generates the input image signal $S_C$ including an image to which each of the RGB color components is added. However, it may be possible to generate the input image signal $S_C$ with an YCbCr color space including a luminance (Y) component and a color difference component based on the color space YCbCr, or it may be possible to generate the input image signal $S_C$ having color components and luminance components by using an HSV color space constituted of three components of color phase (Hue), saturation (Saturation Chroma), and brightness (Value Lightness Brightness), an L*a*b* color space using a three-dimensional space, or the like.

Furthermore, in the first and second embodiments as described above, it has been explained that the compression processing unit 33 and the signal processing unit 35 are independent components. However, the signal processing unit 35 may perform the tone compression process on the base component signal $S_B$. In other words, it may be possible to configure the compression processing unit 33 and the signal processing unit 35 using a shared CPU, and cause the signal processing unit 35 to perform signal processing in accordance with a mode, for example. In this case, the endoscope systems 1 and 1A do not include the compression processing unit 33, and the base component signal $S_B$ divided by the dividing unit 32 is input to the signal processing unit 35. The signal processing unit 35 performs the tone compression process on the input base component signal $S_B$, and inputs the base component signal $S_B$ to the synthesizing unit 34.

Moreover, in the first and second embodiments as described above, it has been explained that an illumination/imaging system using simultaneous lighting is adopted, in which the light source unit 3a emits white light and the light-receiving unit 244a receives light of each of the RGB color components. However, it may be possible to adopt an illumination/imaging system using sequential lighting, in which the light source unit 3a sequentially emits light of a wavelength band of each of the RGB color components, and the light-receiving unit 244a receives light of each of the color components.

Furthermore, in the first and second embodiments as described above, it has been explained that the light source unit 3a is configured separately from the endoscope 2. However, it may be possible to provide a light source device on the endoscope 2 in such a manner that a semiconductor light source is provided at a distal end of the endoscope 2, for example. In addition, it may be possible to add functions of the processing apparatus 3 to the endoscope 2.

Moreover, in the first and second embodiments as described above, it has been explained that the light source unit 3a is integrated with the processing apparatus 3. However, the light source unit 3a and the processing apparatus 3 may be separated from each other, and the illumination unit 301 and the illumination control unit 302 may be provided outside the processing apparatus 3, for example.

Furthermore, in the first and second embodiments as described above, it has been explained that the image signal processing apparatus according to the present disclosure functions as the dividing unit 32, the compression processing unit 33, and the synthesizing unit 34 of the endoscope system 1 using the flexible endoscope 2 for observing body tissue or the like inside a subject, but may be adopted to an endoscope system using a rigid endoscope, an industrial endoscope for observing properties of materials, a capsule endoscope, a fiberscope, or an optical endoscope, such as an optical viewing tube, that is provided with a camera head connected to an eyepiece portion thereof. The image signal processing apparatus according to the present disclosure may be adopted inside and outside of body, and performs the dividing process, the tone compression process, and the synthesizing process on a video signal including an imaging signal and an image signal generated externally.

Moreover, in the first and second embodiments as described above, the endoscope system has been explained as one example. However, the present disclosure may be adopted when video is output to an electronic view finder (EVF) provided on a digital still camera or the like, for example.

Furthermore, in the first and second embodiments as described above, the functions of each of the blocks may be implemented by a single chip or implemented separately by a plurality of chips. If the functions of each of the blocks are separated into the plurality of chips, some of the chips may be provided on a different casing, or functions implemented by some of the chips may be provided on a cloud server.

As described above, the image signal processing apparatus, the image signal processing method, and the image signal processing program according to the present disclosure are useful for generating an image in which a change in colors are prevented and which has good visibility even when tone compression is performed.

REFERENCE SIGNS LIST

According to the present disclosure, it is possible to generate an image with good visibility while preventing a change in colors even when tone compression is performed.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image signal processing apparatus comprising:
   circuitry including:
   an imaging signal acquiring circuitry configured to
      after white light generated by a light source circuitry is emitted to a subject from a tip portion of an endoscope, acquire an imaging signal that is generated by an imaging element provided on the endoscope by receiving light reflected from the subject, and
      generate an input image signal including a base component and a detail component based on the imaging signal;
   a mode setting circuitry configured to change a mode to one of a first mode and a second mode for outputting the input image signal output from the imaging signal acquiring circuitry to different destinations;
   a dividing circuitry configured to
      acquire the input image signal when the mode setting circuitry sets the first mode, and
      divide the input image signal into a base component signal and a detail component signal;
   a first tone compressing circuitry configured to
      acquire the base component signal divided by the dividing circuitry, and
      perform a tone compression process on the base component signal to generate a compressed base component signal;
   a synthesizing circuitry configured to generate a synthetic image signal based on the detail component signal divided by the dividing circuitry and the compressed base component signal generated by the first tone compressing circuitry; and
   a second tone compressing circuitry configured to
      acquire the input image signal when the mode setting circuitry sets a second mode, and
      perform a tone compression process such that tone of the input image signal becomes approximately equal to tone of the compressed base component signal generated by the first tone compressing circuitry.

2. The image signal processing apparatus according to claim 1, wherein the detail component is obtained by dividing the input image signal by the base component.

3. The image signal processing apparatus according to claim 1, wherein
   the input image signal includes color components of red, green, and blue,
   the dividing circuitry is configured to divide the base component signal and the detail component signal for each of the color components, and
   each of the first tone compressing circuitry and the second tone compressing circuitry is configured to perform a tone compression process for each of the color components based on a set parameter.

4. The image signal processing apparatus according to claim 1, further comprising:
a highlighting processing circuitry configured to perform a highlighting process on the detail component signal among component signals divided by the dividing circuitry, wherein
the synthesizing circuitry is configured to generate the synthetic image signal by synthesizing the detail component subjected to the highlighting process and the compressed base component signal subjected to the tone compression process by the first tone compressing circuitry.

5. The image signal processing apparatus according to claim 1, wherein the first tone compressing circuitry and the second tone compressing circuitry are constituted by a shared CPU.

6. An image signal processing method comprising:
acquiring, after white light generated by a light source unit is emitted to a subject from a tip portion of an endoscope, an imaging signal including a base component and a detail component, the imaging signal that is generated by an imaging element provided on the endoscope by receiving light reflected from the subject;
generating an input image signal including a base component and a detail component on the basis of the imaging signal;
changing a mode to one of a first mode and a second mode for outputting the input image signal to different destinations;
acquiring, by a dividing unit, the input image signal when the first mode is set, and dividing the input image signal into a base component signal and a detail component signal when a second mode different from the first mode is set;
performing, by a first tone compressing unit, a tone compression process on the base component signal to generate a compressed base component signal;
generating a synthetic image signal based on the detail component signal and the compressed base component signal; and
acquiring, by a second tone compressing unit, the input image signal when the second mode is set, and performing a tone compression process such that tone of input image signal becomes approximately equal to tone of the compressed base component signal.

7. A non-transitory computer-readable recording medium with an executable program stored thereon, the program causing a computer to execute:
acquiring, after white light generated by a light source unit is emitted to a subject from a tip portion of an endoscope, an imaging signal including a base component and a detail component, the imaging signal that is generated by an imaging element provided on the endoscope by receiving light reflected from the subject;
generating an input image signal including a base component and a detail component on the basis of the imaging signal;
changing a mode to one of a first mode and a second mode for outputting the input image signal to different destinations;
acquiring, by a dividing unit, the input image signal when the first mode is set, and dividing the input image signal into a base component signal and a detail component signal when a second mode different from the first mode is set;
performing, by a first tone compressing unit, a tone compression process on the base component signal to generate a compressed base component signal;
generating a synthetic image signal based on the detail component signal and the compressed base component signal; and
acquiring, by a second tone compressing unit, the input image signal when the second mode is set, and performing a tone compression process such that tone of input image signal becomes approximately equal to tone of the compressed base component signal.

* * * * *